US011559242B2

(12) United States Patent
Badie et al.

(10) Patent No.: US 11,559,242 B2
(45) Date of Patent: Jan. 24, 2023

(54) METHODS AND SYSTEMS FOR DISTINGUISHING OVER-SENSED R-R INTERVALS FROM TRUE R-R INTERVALS

(71) Applicant: Pacesetter, Inc., Sylmar, CA (US)

(72) Inventors: Nima Badie, Berkeley, CA (US); Fujian Qu, San Jose, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 276 days.

(21) Appl. No.: 17/153,036

(22) Filed: Jan. 20, 2021

(65) Prior Publication Data
US 2021/0236041 A1 Aug. 5, 2021

Related U.S. Application Data

(60) Provisional application No. 62/967,913, filed on Jan. 30, 2020.

(51) Int. Cl.
*A61B 5/00* (2006.01)
*A61B 5/352* (2021.01)
*A61B 5/0245* (2006.01)

(52) U.S. Cl.
CPC ............ *A61B 5/352* (2021.01); *A61B 5/0245* (2013.01); *A61B 5/686* (2013.01)

(58) Field of Classification Search
CPC ....... A61B 5/352; A61B 5/0245; A61B 5/686; A61B 5/353; A61B 5/355; A61B 5/36;
(Continued)

(56) References Cited

U.S. PATENT DOCUMENTS 5,755,739 A 5/1998 Sun et al.
6,671,548 B1 12/2003 Mouchawar et al.
(Continued)

FOREIGN PATENT DOCUMENTS

EP 1615693 B1 1/2011
EP 2079520 B1 11/2013
(Continued)

OTHER PUBLICATIONS

International Search Report & the Written Opinion of the International Searching Authority dated Mar. 31, 2021, International Application No. PCT/US2021/014332.
(Continued)

*Primary Examiner* — Scott M. Getzow
(74) *Attorney, Agent, or Firm* — Vierra Magen Marcus LLP

(57) ABSTRACT

Described herein are methods, devices, and systems that monitor heart rate and/or for arrhythmic episodes based on sensed intervals that can include true R-R intervals as well as over-sensed R-R intervals. True R-R intervals are initially identified from an ordered list of the sensed intervals by comparing individual sensed intervals to a sum of an immediately preceding two intervals, and/or an immediately following two intervals. True R-R intervals are also identified by comparing sensed intervals to a mean or median of durations of sensed intervals already identified as true R-R intervals. Individual intervals in a remaining ordered list of sensed intervals (from which true R-R intervals have been removed) are classified as either a short interval or a long interval, and over-sensed R-R intervals are identified based on the results thereof. Such embodiments can be used, e.g., to reduce the reporting of and/or inappropriate responses to false positive tachycardia detections.

20 Claims, 6 Drawing Sheets

(58) Field of Classification Search
CPC ..... A61B 5/361; A61B 5/6869; A61B 5/7217; A61B 5/7275; A61B 5/7282; A61N 1/3621; A61N 1/3925
See application file for complete search history.

(56) References Cited

U.S. PATENT DOCUMENTS

| | | |
|---|---|---|
| 7,027,858 B2 | 4/2006 | Cao et al. |
| 7,155,282 B1 | 12/2006 | Min et al. |
| 7,167,747 B2 | 1/2007 | Gunderson et al. |
| 7,218,966 B2 | 5/2007 | Haefner |
| 7,266,409 B2 | 9/2007 | Gunderson |
| 7,283,863 B2 | 10/2007 | Gunderson et al. |
| 7,333,855 B2 | 2/2008 | Gunderson et al. |
| 7,412,282 B2 | 8/2008 | Houben |
| 7,537,569 B2 | 5/2009 | Sarkar et al. |
| 7,567,835 B2 | 7/2009 | Gunderson et al. |
| 7,582,061 B2 | 9/2009 | Li et al. |
| 7,623,911 B2 | 11/2009 | Sarkar et al. |
| 7,630,756 B2 | 12/2009 | Linker |
| 7,634,310 B2 | 12/2009 | Lee et al. |
| 7,774,049 B2 | 8/2010 | Ghanem et al. |
| 7,774,062 B2 | 8/2010 | Kim et al. |
| 7,783,354 B2 | 8/2010 | Gunderson |
| 7,818,056 B2 | 10/2010 | Kim et al. |
| 7,831,301 B2 | 11/2010 | Cao et al. |
| 7,894,893 B2 | 2/2011 | Kim et al. |
| 7,912,545 B2 | 3/2011 | Li et al. |
| 8,078,277 B2 | 12/2011 | Gunderson et al. |
| 8,160,686 B2 | 4/2012 | Allavatam et al. |
| 8,260,404 B1 | 9/2012 | Bharmi et al. |
| 8,265,737 B2 | 9/2012 | Warren et al. |
| 8,406,872 B2 | 3/2013 | Stadler et al. |
| 8,437,840 B2 | 5/2013 | Patel et al. |
| 8,437,851 B2 | 5/2013 | Corbucci et al. |
| 8,473,042 B2 | 6/2013 | McCarthy et al. |
| 8,506,500 B2 | 8/2013 | Li et al. |
| 8,521,281 B2 | 8/2013 | Patel et al. |
| 8,538,524 B2 | 9/2013 | Rosenberg et al. |
| 8,560,058 B2 | 10/2013 | Babaeizadeh et al. |
| 8,560,069 B2 | 10/2013 | Zhang |
| 8,577,455 B2 | 11/2013 | Mitrani et al. |
| 8,583,221 B1 | 11/2013 | Patel et al. |
| 8,588,895 B2 | 11/2013 | Sanghera et al. |
| 8,588,896 B2 | 11/2013 | Allavatam et al. |
| 8,626,280 B2 | 1/2014 | Allavatam et al. |
| 8,639,316 B2 | 1/2014 | Sarkar |
| 8,744,559 B2 | 6/2014 | Houben et al. |
| 8,750,994 B2 | 6/2014 | Ghosh et al. |
| 8,774,909 B2 | 7/2014 | Patel et al. |
| 8,781,585 B2 | 7/2014 | Gunderson et al. |
| 8,792,971 B2 | 7/2014 | Gunderson et al. |
| 8,886,296 B2 | 11/2014 | Patel |
| 8,897,863 B2 | 11/2014 | Linker |
| 8,914,106 B2 | 12/2014 | Charlton et al. |
| 8,942,793 B2 | 1/2015 | Eberle et al. |
| 9,101,278 B2 | 8/2015 | Fischell et al. |
| 9,167,747 B1 | 10/2015 | Andros et al. |
| 9,307,920 B2 | 4/2016 | Mahajan et al. |
| 9,314,210 B2 | 4/2016 | Li |
| 9,339,662 B2 | 5/2016 | Allavatam et al. |
| 9,381,370 B2 | 7/2016 | Gunderson |
| 9,468,766 B2 | 10/2016 | Sheldon et al. |
| 9,597,525 B2 | 3/2017 | Cao et al. |
| 9,675,261 B2 | 6/2017 | Cao et al. |
| 9,682,238 B2 | 6/2017 | Zhang et al. |
| 9,724,007 B2 | 8/2017 | Cole |
| 9,962,100 B2 | 5/2018 | Allavatam et al. |
| 9,993,653 B2 | 6/2018 | Bardy et al. |
| 9,999,368 B2 | 6/2018 | Perschbacher et al. |
| 10,004,418 B2 | 6/2018 | Cao et al. |
| 10,183,171 B2 | 1/2019 | Ostroff et al. |
| 10,328,274 B2 | 6/2019 | Zhang et al. |
| 10,548,499 B2 | 2/2020 | Bayasi et al. |
| 10,576,288 B2 | 3/2020 | Cao et al. |
| 10,582,870 B2 | 3/2020 | Allavatam et al. |
| 10,702,180 B2 | 7/2020 | Perschbacher et al. |
| 10,709,379 B2 | 7/2020 | Warren et al. |
| 2003/0204215 A1 | 10/2003 | Gunderson et al. |
| 2007/0023294 A1 | 10/2007 | Stadler et al. |
| 2008/0161870 A1 | 7/2008 | Gunderson |
| 2010/0280567 A1 | 11/2010 | Gunderson |
| 2015/0045682 A1 | 2/2015 | Sanghera et al. |
| 2018/0264258 A1 | 9/2018 | Cheng et al. |
| 2018/0318588 A1 | 11/2018 | Dennis |
| 2019/0329038 A1 | 10/2019 | Rhude |
| 2020/0100694 A1 | 4/2020 | Sarkar et al. |

FOREIGN PATENT DOCUMENTS

| | | |
|---|---|---|
| EP | 1877137 B1 | 10/2014 |
| EP | 2967402 B1 | 1/2016 |
| EP | 2364107 B1 | 9/2016 |
| EP | 1219237 B1 | 2/2017 |
| EP | 3247453 B1 | 11/2017 |
| EP | 2895063 B1 | 1/2019 |
| EP | 3422934 B1 | 1/2019 |
| EP | 3432774 B1 | 1/2019 |
| EP | 3566746 A1 | 5/2019 |
| EP | 3592419 B1 | 1/2020 |
| EP | 2741662 B1 | 3/2021 |
| WO | WO03/092810 A2 | 11/2003 |
| WO | WO2019/075529 A1 | 4/2019 |

OTHER PUBLICATIONS

U.S. Appl. No. 17/723,207, filed Apr. 18, 2022.
U.S. Appl. No. 17/745,260, filed May 16, 2022.
"Spontaneous T-wave oversensing," Cardiocases, Pacing & Defibrillation, [https://www.cardiocases.com/en/pacingdefibrillation/clinical-situation/icd/spontaneous-t-wave-oversensing], downloaded Jun. 1, 2021, 9 pages.
U.S. Appl. No. 17/223,885, filed Apr. 6, 2021.
Hadjileontiadis, Leontios J., et al., "Performance of Three QRS Detection Algorithms During Sleep: A Comparative Study," 2001 Proceedings of the 23rd Annual EMBS International Conference, Oct. 25-28, 2001, 4 pages.
Pandit, Diptangshu, et al., "A lightweight QRS detector for single lead ECG signals using a max-min difference algorithm," Computer Methods and Programs in Biomedicine, 144, Feb. 2017 15 pages.
Extended European Search Report dated Oct. 19, 2021, European Patent Application No. 21170198.2-1132.
Response to Extended European Search Report dated Feb. 4, 2022, European Patent Application No. 21170198.2-1132.

METHODS AND SYSTEMS FOR DISTINGUISHING OVER-SENSED R-R INTERVALS FROM TRUE R-R INTERVALS

PRIORITY CLAIMS

This application claims priority to U.S. Provisional Patent Application No. 62/967,913, filed Jan. 30, 2020, which is incorporated herein by reference.

FIELD OF TECHNOLOGY

Embodiments described herein relate to analysis of an electrogram (EGM) or electrocardiogram (ECG), and more specifically, to identifying P-wave and T-wave oversensing, and more generally, to distinguishing true R-R intervals from over-sensed R-R intervals.

BACKGROUND

Various types of implantable medical devices (IMDs) are used to monitor for cardiac arrhythmias. Some types of IMDs, such as implantable cardiac pacemakers and implantable cardiac defibrillators (ICDs), are capable of providing appropriate therapy in response to detected cardiac arrhythmias. Other types of IMDs, such as insertable cardiac monitors (ICMs), are used for diagnostic purposes. ICMs have been increasingly used to diagnose cardiac arrhythmias, particularly atrial fibrillation (AF).

Atrial Fibrillation (AF) is a very common type of supraventricular tachycardia (SVT) which leads to approximately one fifth of all strokes, and is the leading risk factor for ischemic stroke. However, AF is often asymptomatic and intermittent, which typically results in appropriate diagnosis and/or treatment not occurring in a timely manner. To overcome this, many cardiac devices, such as ICMs, now monitor for AF by obtaining an electrogram (EGM) signal and measuring R-R interval variability based on the EGM signal. For example, an ICM or other IMD can compare measures of R-R interval variability to a variability threshold, to automatically detect AF when the variability threshold is exceeded. Indeed, ICMs predominantly identify AF by quantifying the variability in R-R intervals (i.e., by quantifying the variability in the timing of ventricular contractions).

There are a few ICMs that are commercially available, including the Confirm Rx™ ICM, manufactured by Abbott Laboratories, of Chicago, Ill., the Reveal LINQ™ ICM, manufactured by Medtronic, Inc., of Minneapolis, Minn., and the BioMonitor™ 2 (AF and S versions), manufactured by Biotronik SE & Co. KG, of Berlin, Germany. When an ICM detects an episode of AF, information about the episode may be recorded and a corresponding EGM segment (and/or other information) can be transmitted from the ICM to a patient care network for clinician review. False positive AF detections are highly undesirable, as the burden of sorting through large numbers of clinically irrelevant episodes of AF can be time consuming and costly.

In various IMDs, such as ICMs, clinicians are provided with the capability of programming an R-wave sensing threshold, to which samples of an EGM are compared to detect R-waves in the EGM. Clinicians often use relatively low R-wave sensing thresholds in order to reduce the undersensing of low amplitude R-waves. However, R-wave amplitudes may vary in real-life settings due to various reasons including physical activity and posture changes. If the R-wave sensing threshold is programmed to be too low (i.e., too sensitive), then lower amplitude features of the EGM (e.g. P-waves, T-waves, and/or noise) may be incorrectly sensed as R-waves. Unfortunately, false positive AF detections caused by oversensing higher-amplitude P-waves or T-waves (rather than just R-waves) are common, resulting in low AF detection specificity. Moreover, presently available P-wave and T-wave detection discriminator techniques are often unable or inadequate to correctly distinguish P-waves and T-waves from R-waves. Accordingly, there is a still a need for improved techniques for distinguishing P-waves and T-waves from R-waves, and for distinguishing over-sensed R-R intervals from true R-R intervals.

SUMMARY

Certain embodiments of the present technology are directed to methods, devices, and systems that monitor HR and/or for one or more types of arrhythmic episodes based on sensed intervals that can include true R-R intervals as well as over-sensed R-R intervals. Such a method can include: obtaining an ordered list of sensed intervals, wherein each of the sensed intervals has a respective duration; identifying as a true R-R interval, each said sensed interval having a duration that is within a first specified threshold of either (i) a sum of the durations of an immediately preceding two intervals in the ordered list of sensed intervals, or (ii) a sum of the durations of an immediately following two intervals in the ordered list of sensed intervals; and identifying as a true R-R interval, each said sensed interval having a duration that is within a second specified threshold of a mean or median of the durations of the sensed intervals already identified as true R-R intervals, wherein the second specified threshold may or may not be the same as the first specified threshold. The method can also include: removing, from the ordered list of sensed intervals, each of the sensed intervals that was identified as being a true R-R interval, to thereby produce a remaining ordered list of sensed intervals; classifying individual intervals in the remaining ordered list of sensed intervals as either a short interval or a long interval; and identifying one or more over-sensed R-R intervals, in the remaining ordered list of sensed intervals, based on results of the classifying individual intervals in the remaining ordered list of sensed intervals as either a said short interval or a said long interval.

In accordance with certain embodiments, a short interval (in the remaining ordered list of sensed intervals) is identified (aka classified) as an over-sensed R-R interval when all of the following are true: (1) a difference between a duration of the sensed interval that was classified as a said short interval and a duration of an immediately preceding sensed interval that was classified as a said short interval is within a third specified threshold; (2) a difference between the duration of the sensed interval that was classified as a said short interval and a duration of an immediately following sensed interval that was classified as a said long interval is greater than a fourth specified threshold; and (3) the duration the sensed interval that was classified as a said short interval is less than a fifth specified threshold.

In accordance with certain embodiments, a long interval (in the remaining ordered list of sensed intervals) is identified (aka classified) as an over-sensed R-R interval if an immediately preceding or following adjacent sensed interval classified as a said short interval has been identified as an over-sensed R-R interval.

In accordance with certain embodiments, the method further comprises: determining an oversensing score based on how many of the sensed intervals classified as a said short interval were identified as being an over-sensed R-R interval; and determining that a detected AF episode or other type of arrhythmic episode was a false positive detection when the oversensing score exceeds a specified oversensing threshold. In accordance with certain embodiments, the specified oversensing threshold comprises a specified percentage threshold, the oversensing score comprises what percentage of all of the sensed intervals classified as a said short interval were identified as being an over-sensed R-R interval, and a detected AF episode or other type of arrhythmic episode is determined to be a false positive detection when the determined percentage exceeds the specified percentage threshold.

In accordance with certain embodiments, such a method is performed by an IMD in response to an AF episode or other type of arrhythmic episode being detected by the IMD, and the method further comprises the IMD determining, based on results of the steps summarized above, whether the AF episode or other type of arrhythmic episode that was detected by the IMD was a false positive detection. Such an IMD can be, for example, an insertable cardiac monitor (ICM), a cardiac pacemaker to which one or more leads is/are attached, a leadless cardiac pacemaker (LCP), or an implantable cardioverter defibrillator (ICD).

In accordance with certain embodiments, the IMD is configured to transmit, to an external device that is communicatively coupled to a patient care network, data corresponding to an AF episode or other type of arrhythmic episode that is detected by the IMD. In such an embodiment, the method can further comprise the IMD preventing the transmitting, to the external device that is communicatively coupled to the patient care network, data corresponding to an AF episode or other type of arrhythmic episode that is detected by the IMD but is thereafter determined by the IMD as being a false positive detection. Alternatively, data corresponding to a limited amount of AF episodes or other type of arrhythmic episodes that is/are detected by the IMD but is/are thereafter determined by the IMD as being a false positive detection can be transmitted to a patient care network so that such data can be used by a clinician to adjust an R-wave sensing threshold.

In accordance with certain embodiments the ordered list of sensed intervals is obtained by: obtaining an electrogram (EGM) segment corresponding to a period of time preceding and leading up to the AF episode or other type of arrhythmic episode that was detected; identifying potential R-waves within the EGM segment; and determining intervals between consecutive ones of the potential R-waves to thereby produce the ordered list of sensed intervals.

In accordance with certain embodiments, the classifying individual intervals, in the remaining ordered list of sensed intervals, as either a short interval or a long interval comprises: classifying a said interval, in the remaining ordered list of sensed intervals, as a short interval when a duration of the said interval is shorter than an immediately following interval in the remaining ordered list of sensed intervals; and classifying a said interval, in the remaining ordered list of sensed intervals, as a long interval when a duration of the said interval is longer than an immediately following interval in the remaining ordered list of sensed intervals.

In accordance with certain embodiments, steps summarized above are performed by a device that monitors heart rate (HR) based on intervals identified from a segment of an electrogram (EGM) or electrocardiogram (ECG), and the method further comprises: the device determining, based on results of steps summarized above, whether a monitored HR is inaccurate due to oversensing and thus should be ignored or recalculated.

In accordance with certain embodiments, the method further comprises, after identifying true R-R intervals and identifying over-sensed R-R intervals: combining pairs of over-sensed R-R intervals to identify further true R-R intervals; producing a corrected ordered list of sensed intervals that includes the true R-R intervals (initially identified without any combining) and includes the further true R-R intervals identified by combining pairs of over-sensed R-R intervals; and monitoring HR and/or for an arrhythmic episode based on the corrected ordered list of sensed intervals.

In accordance with certain embodiments, a device comprises: one or more electrodes; a sensing circuitry coupled to the one or more electrodes and configured to obtain a signal indicative of electrical activity of the patient's heart; and at least one of a processor or controller. The at least one of a processor or controller is configure to: obtain an ordered list of sensed intervals, based on the signal indicative of electrical activity of the patient's heart, wherein each of the sensed intervals has a respective duration; identify as a true R-R interval, each said sensed interval having a duration that is within a first specified threshold of either (i) a sum of the durations of an immediately preceding two intervals in the ordered list of sensed intervals, or (ii) a sum of the durations of an immediately following two intervals in the ordered list of sensed intervals; and identify as a true R-R interval, each said sensed interval having a duration that is within a second specified threshold of a mean or median of the durations of the sensed intervals already identified as true R-R intervals, wherein the second specified threshold may or may not be the same as the first specified threshold. The at least one of a processor or controller is/are also configured to: remove, from the ordered list of sensed intervals, each of the sensed intervals that was identified as being a true R-R interval, to thereby produce a remaining ordered list of sensed intervals; classify individual intervals, in the remaining ordered list of sensed intervals, as either a short interval or a long interval; and identify one or more over-sensed R-R intervals, in the remaining ordered list of sensed intervals, based on an analysis of at least the short intervals in the remaining ordered list of sensed intervals. Such a device can be an ICM, a cardiac pacemaker to which one or more leads is/are attached, an LCP, or an ICD.

In accordance with certain embodiments, the at least one of a processor or controller is/are further configured to: determine an oversensing score based on how many of the sensed intervals classified as a said short interval were identified as being an over-sensed R-R interval; and determine, based on the oversensing score, whether a detected AF episode or other type of arrhythmic episode was a false positive detection.

In accordance with certain embodiments, the at least one of a processor or controller is/are further configured to: combine pairs of over-sensed R-R intervals to identify further true R-R intervals; produce a corrected ordered list of sensed intervals including true R-R intervals, at least some of which are identified by combining pairs of over-sensed R-R intervals; and monitor heart rate and/or for an arrhythmic episode based on the corrected ordered list of sensed intervals.

In accordance with certain embodiment, the device further comprises a transceiver configured to wireless communicate with an external device. Also, the at least one of a processor or controller is/are further configured to interact with the transceiver to: cause data corresponding to an AF episode or other type of arrhythmic episode that is detected by the device be selectively transmitted to the external device; and prevent data corresponding to an AF episode or other type of arrhythmic episode that is detected by the device, but is thereafter determined by the device as being a false positive detection, from being transmitted to the external device.

In accordance with certain embodiments of the present technology, a method comprises: identifying true R-R intervals within an ordered list of sensed intervals and removing from the ordered list of sensed intervals each of the sensed intervals that was identified as being a true R-R interval, to thereby produce a remaining ordered list of sensed intervals; classifying individual intervals, in the remaining ordered list of sensed intervals, as either a short interval or a long interval; identifying which individual intervals, which have been classified as a said short interval, are over-sensed R-R intervals; and determining, based on results the identifying which individual intervals are over-sensed R-R intervals, whether a monitored heart rate or arrhythmic episode detection is inaccurate due to oversensing and thus should be ignored or recalculated.

In accordance with certain embodiments, the determining, based on results the identifying which individual intervals are over-sensed R-R intervals, whether a monitored heart rate or arrhythmic episode detection is inaccurate due to oversensing and thus should be ignored or recalculated, comprises: determining an oversensing score based on how many of the sensed intervals classified as a said short interval were identified as being an over-sensed R-R interval; and determining, based on the oversensing score, whether a monitored heart rate of arrhythmic episode detection is inaccurate due to oversensing and thus should be ignored or recalculated.

In accordance with certain embodiments, after there is a determination that a monitored heart rate or arrhythmic episode detection is inaccurate due to oversensing and thus should be ignored or recalculated, the method further comprises: combining pairs of over-sensed R-R intervals to identify further true R-R intervals; producing a corrected ordered list of sensed intervals including true R-R intervals, at least some of which are identified by combining pairs of over-sensed R-R intervals; and monitoring heart rate and/or for an arrhythmic episode based on the corrected ordered list of sensed intervals.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1:
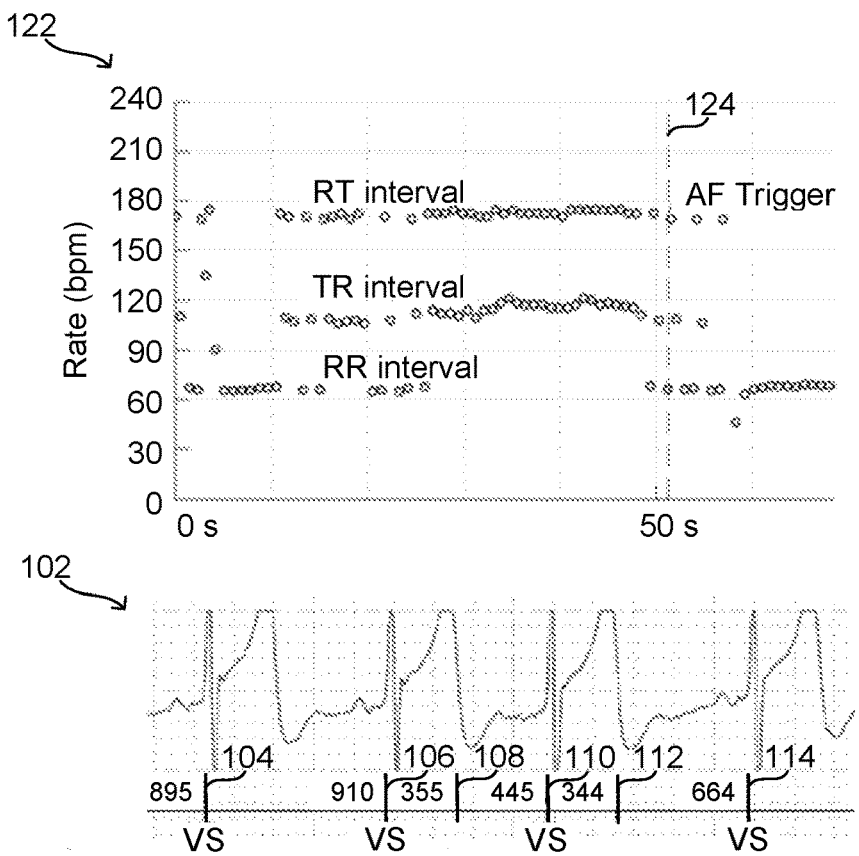
FIG. 1 includes a portion of an EGM segment that resulted in an atrial AF detection due to over-sensed T-waves and includes a graph of HR versus time.

It is well known that each cardiac cycle represented within an EGM or ECG typically includes a P-wave, followed by a QRS complex, followed by a T-wave, with the QRS complex including Q-, R-, and S-waves. The P-wave is caused by depolarization of the atria. This is followed by atrial contraction, which is indicated by a slight rise in atrial pressure contributing to further filling of the ventricle. Following atrial contraction is ventricular depolarization, as indicated by the QRS complex, with ventricular depolarization initiating contraction of the ventricles resulting in a rise in ventricular pressure until it exceeds the pulmonary and aortic diastolic pressures to result in forward flow as the blood is ejected from the ventricles. Ventricular repolarization occurs thereafter, as indicated by the T-wave and this is associated with the onset of ventricular relaxation in which forward flow stops, the pressure in the ventricle falls below that in the atria at which time the mitral and tricuspid valves open to begin to passively fill the ventricle during diastole. The terms EGM, EGM signal, and EGM waveform are used interchangeably herein. Similarly, the terms ECG, ECG signal, and ECG waveform are used interchangeably herein. Both ECG and EGM signals are signals indicative of electrical activity of a patient's heart.

The R-wave is the largest wave in the QRS complex, and it often identified by comparing samples of an EGM or ECG to an R-wave threshold. Various measurements can be obtained based on the EGM or ECG waveform, including measurements of R-R intervals, where an R-R interval is the duration between a pair of consecutive R-waves. As noted above, in the Background, a common technique for detecting AF is based on measures of R-R interval variability. However, where T-waves and/or P-waves are falsely identified as R-waves, false R-R intervals can be identified which have a high variability, leading to false detections of AF. In other words, over-sensed P-waves and/or over-sensed T-waves can lead to false positive AF detections. An over-sensed P-wave, as the term is used herein, refers to a P-wave that is falsely identified as an R-wave. Similarly, an over-sensed T-wave, as the term is used herein, refers to a T-wave that is falsely identified as an R-wave. An under-sensed R-wave, as the term is used herein, refers to an R-wave that is not detected Certain embodiments of the present technology relate to methods and devices that use sensed intervals to determine whether P-wave and/or T-wave oversensing has occurred, and more generally, to distinguish true R-R intervals from false R-R intervals. These embodiments can beneficially be used, for example, to prevent or reject false positive AF detections before they are transmitted to a clinician, consequently improving AF detection specificity and reducing downstream clinical resources. A true R-R interval, as the term is used herein, refers to an actual R-R interval. A false R-R interval, as the term is used herein, refers to an interval that is mistakenly identified as an R-R interval, but is not an actual R-R interval. Exemplary types of intervals that may be mistakenly identified as an R-R interval, and thus are examples of false R-R intervals, include, but are not limited to, P-R intervals, R-T intervals, P-T intervals, and T-P intervals. A P-R interval can be mistakenly identified as an R-R interval where a P-wave is over-sensed. An R-T interval can be mistakenly identified as R-R interval where a T-wave is over-sensed. A P-T interval or a T-P interval can be mistakenly identified as an R-R interval where T- and P-waves are over-sensed and an R-wave is under-sensed. These are just a few examples of types of false R-R intervals and how they may occur, which examples are not intended to be all inclusive. False R-R intervals are also referred to herein as over-sensed R-R intervals.

Certain embodiments of the present technology described herein rely on the phenomenon that an over-sensed P-wave or an over-sensed T-wave effectively divides a normal R-R interval into two shorter intervals (e.g. an R-T interval and a T-R interval), the sum of which is an actual R-R interval, which can also be referred to as the true R-R interval. Thus, certain embodiments of the present technology identify intervals that are similar to the sum of either the last two intervals or the next two intervals, which are the real R-R intervals, and do not correspond to oversensing. Further analysis (e.g., arrhythmia detection analysis) can then proceed using only the remaining intervals. Of the remaining R-R intervals, intervals are flagged if, looking at the next two intervals, they follow a "short-long-short" pattern, wherein the terms "short" and "long" are relative terms, as both groups of intervals are much shorter than true R-R intervals. Of these flagged intervals, an "oversensing score" can be calculated as the percentage of these intervals which are (i) sufficiently similar in duration to the neighboring flagged intervals, (ii) sufficiently different in duration from the neighboring (unflagged) intervals, and (iii) sufficiently short in duration. This "oversensing score" can be an estimate of the percentage of intervals that either start or end with an over-sensed R-wave. Explained another way, the "oversensing score" can be an estimate of the percentage of short intervals that classified as over-sensed R-R intervals. If the "oversensing score" in the window preceding an AF trigger exceeds a specified threshold (e.g. 50%), then the AF trigger can be associated with oversensing (i.e., false positive AF), and can be rejected. Further and alternative details of such embodiments of the present technology are described below.

In accordance with certain embodiments, a list of potential sensed R-R intervals is obtained for a recorded EGM clip, which can also be referred to as a segment of an EGM, or an EGM segment. Because this list of potential R-R intervals may actually including P-R intervals, R-P intervals, T-R intervals, and/or R-T intervals, due to oversensing of P-waves and/or T-waves, these potential R-R intervals will often be referred to more generally as "intervals" in this document for simplicity. While a large portion of the following description and patient example discussed below describes T-wave oversensing, the same principles apply to P-wave oversensing.

An example of T-wave oversensing is shown if FIG. 1, taken directly from an EGM clip file of a patient having an implanted Confirm RX™ ICM. At the bottom of FIG. 1 is shown a portion of an EGM segment 102 that resulted in an AF detection due to over-sensed T-waves. At the top of FIG. 1 is shown a graph or plot that includes heart rate (HR) in beats per minute (bpm) along the vertical axis, and time in seconds (s) long the horizontal axis. The dashed vertical line 124 corresponds to an AF detection occurring at a point in time corresponding to ~52 seconds, and thus, the vertical line 124 is also marked AF Trigger.

Referring to the portion of the EGM segment 102 shown at the bottom of FIG. 1, actual R-waves in the EGM segment 102 that correspond to actual ventricular sensed (VS) events are marked VS. Next to the first vertical line 104 marked VS is the number 895, referring to an R-R interval of 895 ms. Next to the second vertical line 106 marked VS is the number 910, referring to an R-R interval of 910 ms. Following the second vertical line 106 marked VS is another vertical line 108, which is not marked VS, and actually corresponds to an over-sensed T-wave. Next to the vertical line 108 is the number 355, referring to an R-T interval of 355 ms. Following the vertical line 108 is the vertical line 110 marked VS, which corresponds to a true R-wave. Next to the vertical line 110 is the number 445, referring to a T-R interval of 455 ms. Following the vertical line 110 is the vertical line 112, which corresponds to another over-sensed T-wave. Next to the vertical line 112 is the number 344, referring to an R-T interval of 344 ms. Following the vertical line 112 is the vertical line 114 marked VS, which corresponds to a true R-wave. Next to the vertical line 114 is the number 664, referring to a T-R interval of 664 ms. In summary, the ordered list of intervals obtained from the portion of the EGM segment 102 shown at the bottom of FIG. 1 have intervals of: 895 ms, 910 ms, 355 ms, 445 ms, 344 ms, and 664 ms.

Note that the interval between the vertical line labeled 106 and the vertical line labeled 110 (both marked VS, and thus corresponding to true R-waves) is 900 ms (i.e., 355 ms+445 ms=900 ms). Also note that the interval between the vertical line labeled 110 and the vertical line labeled 114 (both marked VS, and thus corresponding to true R-waves) is 1008 ms (i.e., 344 ms+664 ms=1008 ms). Accordingly, if the over-sensed T-waves (corresponding to the vertical lines 108 and 112) were not detected, then the ordered list of intervals obtained from the portion of the EGM segment 102 shown at the bottom of FIG. 1 would instead have intervals of: 895 ms, 910 ms, 900 ms, and 1008 ms.

In the example shown in FIG. 1, the true R-R intervals are associated with a HR of approximately 65 bpm. Thus, the true R-R intervals are approximately 923 milliseconds (ms), because 60 sec/min divided by 65 bpm=0.923 seconds=923 ms. However, where there are over-sensed T-waves, every over-sensed T-wave results in two shorter intervals with HRs of approximately 110-120 bpm (R-T intervals) and 170-175 bpm (T-R intervals). For an example, where there is an over-sensed T-wave detected between a pair of true R-waves, rather than the list of intervals including a true R-R interval (having a duration of 873 ms), the list can instead include an R-T interval of approximately 520 ms and a T-R interval of approximately 353 ms.

In accordance with certain embodiments, in order to simplify implementation, techniques for identifying P-wave and/or T-wave oversensing are based on intervals, rather than heart rates. However, it is noted that such techniques can alternatively be heart rate based, instead of intervals based, while still being within the scope of the embodiments of the present technology. For the following discussion, such techniques focus on a 30 second window preceding an AF trigger. However, it is noted that windows of other (i.e., longer or shorter) lengths can instead be used while still being within the scope of the embodiments described herein. The AF trigger can be detected in various different manners, such as by analyzing heart rate variability and/or R-R interval variability, but is not limited thereto.

Figure 2:
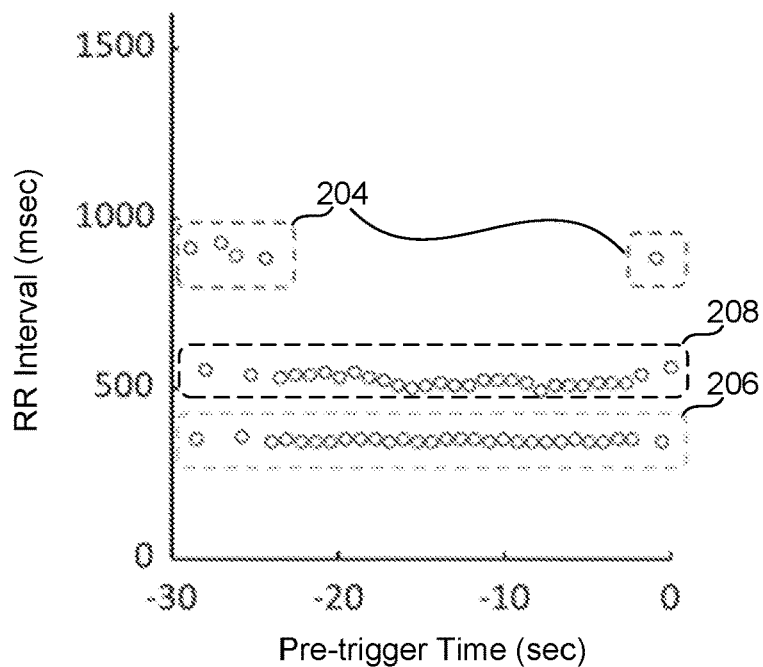
FIG. 2 includes a graph of sensed intervals for a window preceding an AF trigger, which sensed intervals correspond to the inverse of the heart rates shown in FIG. 1.

FIG. 2 illustrates a graph or plot of sensed intervals (in ms) for a 30 ms window preceding an AF trigger, which sensed intervals correspond to the inverse of the heart rates that were shown in FIG. 1. In FIG. 2, the dashed blocks 204 corresponds to sensed intervals that are true R-R intervals, the dashed block 206 corresponds to the shorter of the two groups of over-sensed intervals, and the dashed block 208 corresponds to the longer of the two groups of over-sensed intervals. More specifically, the dashed block 206 corresponds to R-T intervals, and the dashed block 208 corresponds to the T-R intervals.

Where a T-wave is mistakenly detected as an R-wave, it can be said that T-wave oversensing occurred, or that an over-sensed R-wave was detected. As can be appreciated from FIGS. 1 and 2, with every over-sensed R-wave (resulted from T-wave oversensing), the true R-R interval is bisected into two shorter intervals, the sum of which is the true R-R interval. Similarly, where a P-wave is mistakenly detected as an R-wave, it can be said that P-wave oversensing occurred, or that an over-sensed R-wave was detected. If P-wave oversensing occurs (instead of T-wave oversensing), with every over-sensed R-wave (resulted from P-wave oversensing), the true R-R interval is also bisected into two shorter intervals, the sum of which is the true R-R interval.

Certain embodiments of the present technology identify intervals that are not true R-R intervals. In other words, certain embodiments of the present technology identify false R-R intervals, which can also be referred to as over-sensed R-R intervals. Examples of over-sensed R-R intervals include R-T intervals and T-R intervals, as can be appreciated from the above discussion of FIGS. 1 and 2. Other examples of over-sensed R-R intervals include P-R intervals and R-P intervals.

When attempting to identify over-sensed R-R intervals, it is useful to remove true R-R intervals from the list of intervals being analyzed. This can be accomplished by removing all intervals that are within a specified percentage (e.g., 10%) of the sum of either the immediately preceding two or the immediately following two intervals within the list, as such intervals are likely true R-R intervals with a neighboring over-sensed interval. However, depending on how frequently oversensing occurs, a true R-R may not be neighbored by over-sensed R-waves. Thus, R-R intervals are also classified at true R-R intervals and removed from the list if they are within a specified percentage (e.g., 10%) of the median or mean of the previously-removed "true" R-R intervals. Henceforth, the algorithm will rely only on the remaining intervals that were not removed (i.e., questionable R-R intervals) to identify over-sensed R-R intervals.

For the remaining intervals, oversensing would result in a consistent "short-long-short" alternation. In the case of T-wave oversensing, this pattern corresponds to a short R-T interval (ventricular repolarization time) followed by a slightly longer T-R interval (from ventricular repolarization until the next ventricular depolarization). In the case of P-wave oversensing, this pattern corresponds to a short P-R interval (atrioventricular conduction time) followed by a slightly longer R-P interval (from ventricular depolarization until the next atrial depolarization).

To quantify how often this "short-long-short" pattern occurs, each remaining interval is labeled or classified as either "short" (shorter than the next non-removed interval, which next non-removed interval is longer than the following non-removed interval) or "long" (longer than the next non-removed interval, which next non-removed interval is in turn shorter than the following non-removed interval). In other words, interval (i)<interval (i+1), and interval (i+1) >interval (i+2). Note that both the "short" and "long" intervals are both much shorter than the true R-R interval—they are "short" or "long" relative to each other. However, certain rhythms can also produce a short-long-short pattern by happenstance, such as premature atrial contraction and premature ventricular contractions (PACs and PVCs) or AF. Thus, in accordance with certain embodiments, three more discrimination criteria are used to count the number of "short" intervals associated with oversensing. In other words, these discrimination criteria are used to determine whether individual short intervals are over-sensed R-R intervals. Such three additional discrimination criteria, each of which are discussed below, include: short interval variability, short-long interval discrepancy, and short interval duration.

Short Interval Variability—First, during P-wave or T-wave oversensing, the "short" intervals (i.e., P-R interval or R-T interval) should have relatively consistent values, as they depend on either atrioventricular conduction times (P-R) or ventricular repolarization times (R-T). In contrast, the longer intervals (e.g. R-P or T-R) depend on the heart rate, which is much more variable than conduction times or repolarization times. Furthermore, AF or PVCs, which may also demonstrate a "short-long-short" pattern, would result in highly variable "short" interval durations. Therefore, the "short" intervals that truly correspond to oversensing should have low interval-interval variability, quantified by a difference from the previous "short" interval of less than 10%, or some other specified threshold.

Short-Long Interval Discrepancy—The second discrimination criterion serves to discriminate oversensing from R-wave undersensing. During R-wave undersensing, one under-sensed R-wave results in an R-R interval that is similar to the sum of the previous two or next two intervals, effectively appearing as a true R-R interval surrounded by intervals associated with oversensing. However, in the case of undersensing, the "short" and "long" intervals would be almost identical in duration. Therefore, the second discrimination criterion ensures a sufficient discrepancy between the "short" and "long" intervals. Specifically, the "short" intervals that truly correspond to oversensing should differ from the next "long" interval by greater than 5% (or some other specified threshold).

Short Interval Duration—The third discrimination criterion handles the possibility that all of the above criteria could be satisfied by slow, yet variable, heart rates. During true oversensing, however, the "short" intervals should correspond to a very fast heart rate. Thus, the third discrimination criterion requires that the "short" intervals should all have values less 444 ms (i.e., greater than 135 bpm), or some other specified threshold. If the over-sensed R-waves corresponding to these "short" intervals are eliminated, the true R-R intervals can be calculated.

Figure 3:
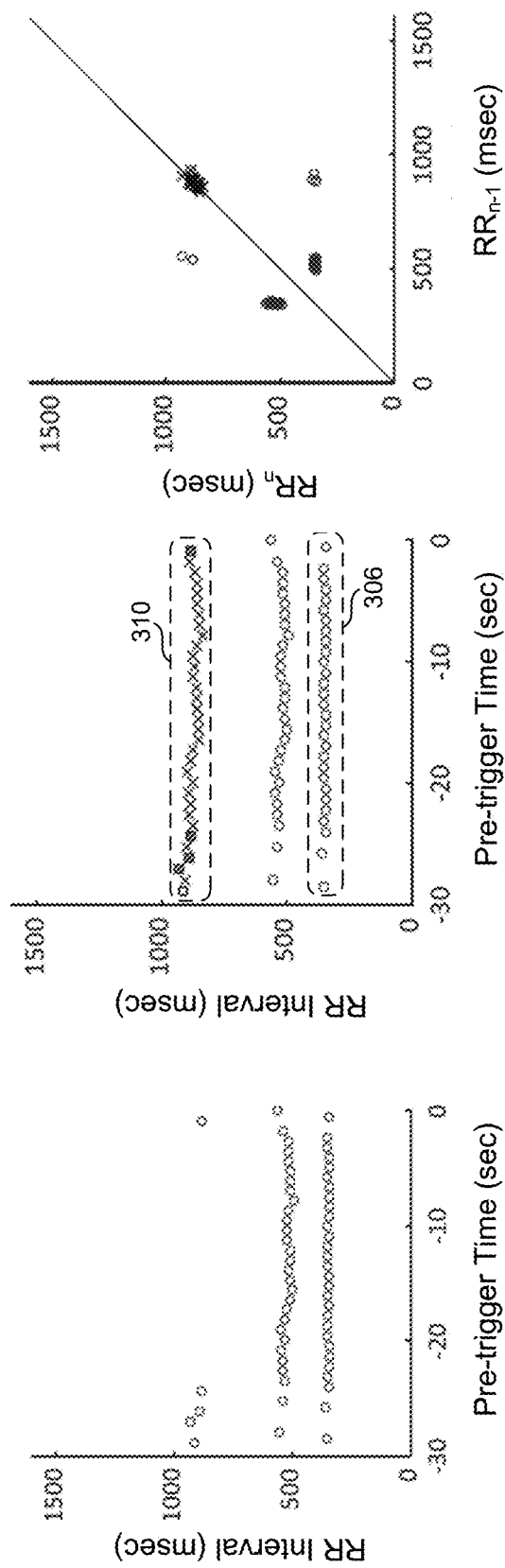
FIG. 3 includes a left panel graph that is the same as FIG. 2, a center panel graph that illustrates how true R-R intervals can be calculated by adding durations of identified R-T and T-R intervals, and a right panel Poincare plot that illustrates actual R-R interval stability after oversensing correction of the present technology is performed.

FIG. 3 illustrates how embodiments of the present technology can be used to impact the example intervals described with references to FIGS. 1 and 2. The left panel in FIG. 3, which is the same as FIG. 2 discussed above, includes true R-R intervals as well as over-sensed R-R intervals (which include R-T intervals and T-R intervals), as was explained above with reference to FIG. 2. Using embodiments of the present technology summarized above, and described in additional detail below, the original sensed intervals (shown in the left panel) are corrected by first removing true R-R intervals. Next, the true "short" over-sensed intervals (the lower horizontal line of circles within the dashed block 306 in the center panel of FIG. 3) are identified. By eliminating the over-sensed R-waves corresponding to these "short" intervals, the true R-R intervals that remain can be calculated, which are shown as Xs within the dashed block 310 (in the center panel of FIG. 3). More specifically, durations of the true R-R intervals represented by the Xs within the dashed block 310 (in the center panel of FIG. 3) are calculated by adding (aka summing) the durations of pairs of sensed intervals that include one short interval (an R-T interval) and one long interval (a T-R interval). Note that calculated (aka corrected) R-R intervals in the center panel in FIG. 3 are consistent with the previously identified and removed true R-R intervals. The Poincare plot (shown in the right panel in FIG. 3) plots the relationship between each interval and the immediately preceding interval, showing the same data and markers as the center panel. This Poincare plot illustrates the actual R-R interval stability (Xs), after oversensing correction of the original R-R intervals (circles) by the present technology is performed. Before oversensing correction, each interval differs, albeit predictably, from the preceding interval. After oversensing correction, all the interval-interval difference is negligible (overlapping Xs).

Additional and alternative details of the embodiments of the present technology, introduced above, are described below with reference to FIGS. 4A, 4B, and 4C, which can be referred to collectively as FIGS. 4A-4C, or even more succinctly as FIG. 4.

Figure 4A:
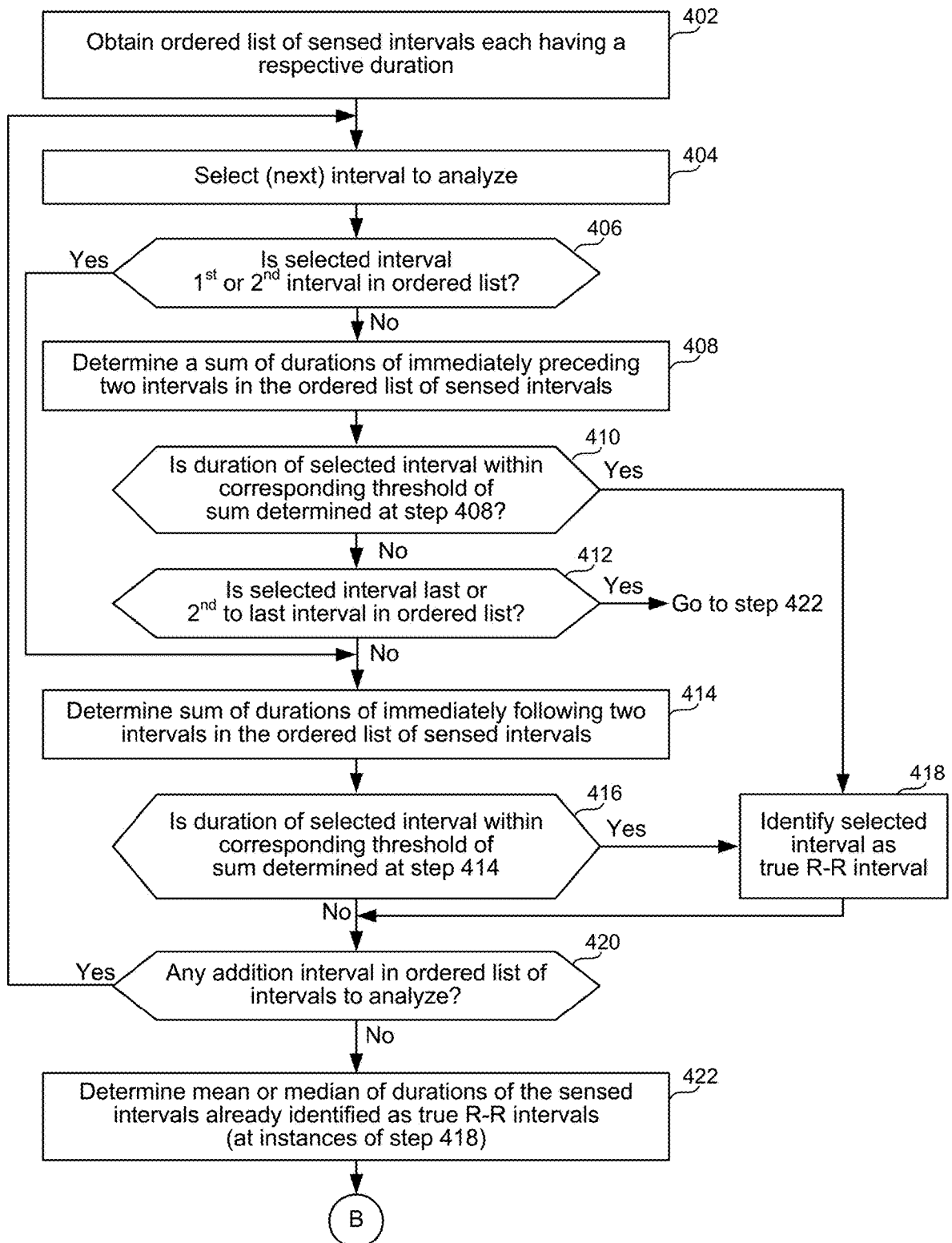
FIGS. 4A, 4B, and 4C, which can be collectively referred to as FIG. 4, includes a high level flow diagram that is used to describe how true R-R intervals can be distinguished from over-sensed R-R intervals using embodiments of the present technology, and how an oversensing score can be determined and used.
Figure 4B:
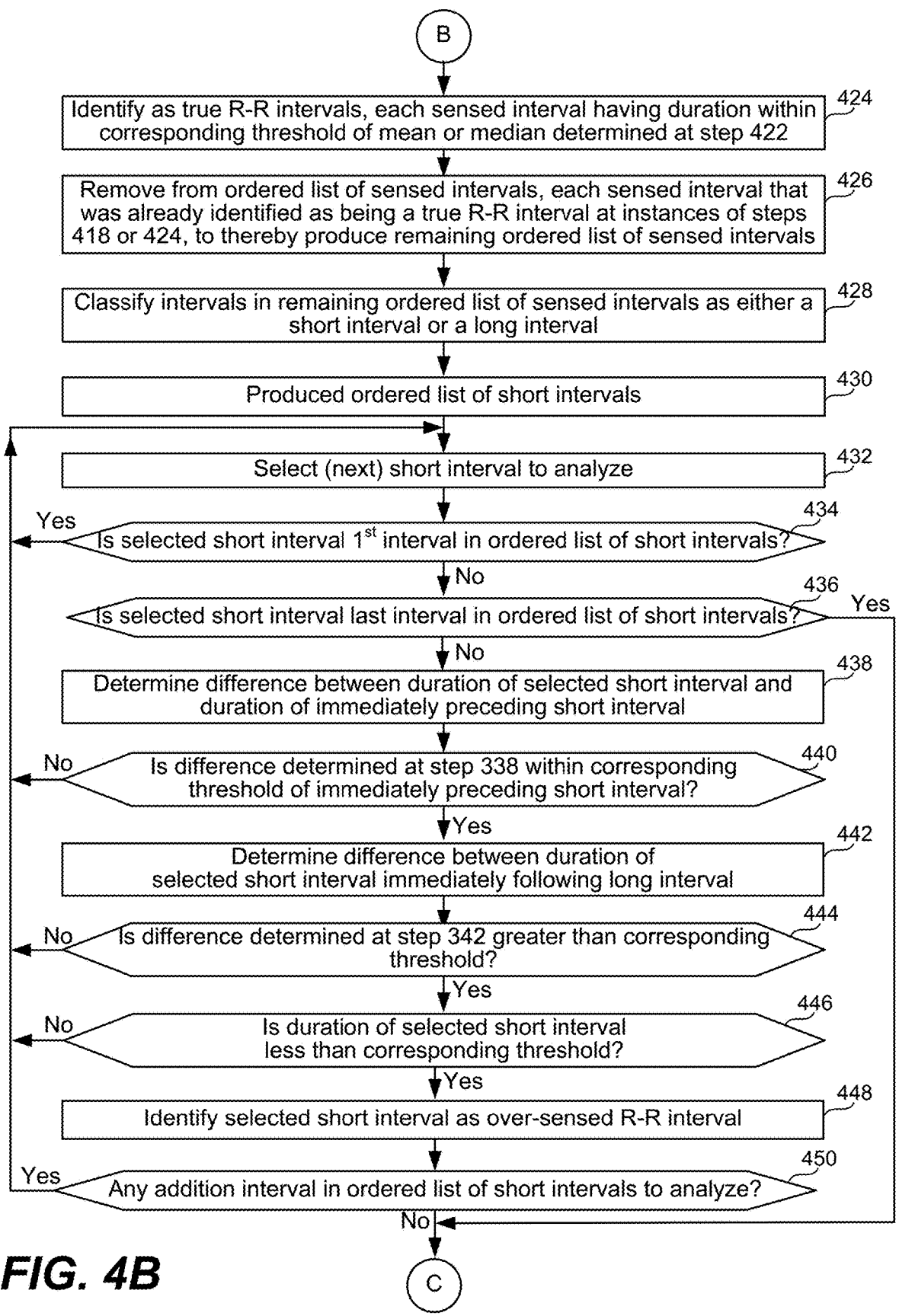

Referring to FIG. 4A, step 402 involves obtaining an ordered list of intervals that each have a respective duration. The ordered list of intervals, obtained at step 402, would preferably include only true R-R intervals. However, due to T-wave and/or P-wave oversensing, the ordered list of intervals obtained at step 402 would likely also include one or more over-sensed R-R intervals. In accordance with certain embodiments, the ordered list of sensed intervals is obtained by sensing or otherwise obtaining an EGM or ECG segment corresponding to a period of time preceding and leading up to an AF episode or other type of arrhythmic episode that was detected, identifying potential R-waves within the EGM or ECG segment, and determining intervals between consecutive ones of the potential R-waves to thereby produce the ordered list of sensed intervals. Such potential R-waves can be identified within the EGM or ECG segment by comparing the EGM segment, or samples thereof, to an R-wave sensing threshold, and identifying potential R-waves when the R-wave sensing threshold is reached or exceeded. Other variations are also possible and within the scope of the embodiments described herein.

Step 404 involves selecting an interval (from the ordered list of intervals obtained at step 402) to analyze. The first time step 404 is performed (for an ordered list of intervals), the first interval in the ordered list is selected. The second time step 404 is performed (for the ordered list of intervals), the second interval in the ordered list is selected, and so on.

At step 406 there is a determination of whether the interval (selected for analysis at step 404) is the first or second interval in the ordered list of intervals. If the selected interval is the first or second interval (i.e., if the answer to the determination at step 406 is Yes), then flow goes to step 414 (thereby skipping steps 408, 410, and 412). If the selected interval is not the first or second interval (i.e., if the answer to the determination at step 406 is No), then flow goes to step 408.

Step 408 involves determining a sum of the durations of the immediately preceding two intervals in the ordered list of sensed intervals. At step 410 there is a determination of whether the duration of the selected interval is within a corresponding threshold (e.g., within 10%) of the sum determined at step 408. If the duration of the selected interval is within the corresponding threshold (e.g., within 10%) of the sum determined at step 408 (i.e., if the answer to the determination at step 410 is Yes), then flow goes to step 418, and the selected interval is identified (aka classified) as a true R-R interval. If the duration of the selected interval is not within the corresponding threshold (e.g., within 10%) of the sum determined at step 408 (i.e., if the answer to the determination at step 410 is No), then flow goes to step 412.

At step 412 there is a determination of whether the selected interval is the last or second to last interval in the ordered list of sensed intervals. If the selected interval is the last or second to last interval (i.e., if the answer to the determination at step 412 is Yes), then flow goes to step 422 (thereby skipping steps 414, 416, and 420). If the selected interval is not the last or second to last interval (i.e., if the answer to the determination at step 412 is No), then flow goes to step 414.

Step 414 involves determining the sum of the durations of the immediately following two intervals in the ordered list of intervals. At step 416 there is a determination of whether the duration of the selected interval is within a corresponding threshold (e.g., within 10%) of the sum determined at step 414. If the duration of the selected interval is within a corresponding threshold (e.g., within 10%) of the sum determined at step 414 (i.e., if the answer to the determination at step 416 is Yes), then flow goes to step 418, and the selected interval is identified (aka classified) as a true R-R interval. If the duration of the selected interval is not within the corresponding threshold (e.g., within 10%) of the sum determined at step 414 (i.e., if the answer to the determination at step 416 is No), then flow goes to step 420.

At step 420 there is a determination of whether there is at least one additional interval (in the ordered list of sensed intervals) to analyze. If the answer to the determination at step 420 is Yes, then flow returns to step 404 where the next interval (in the ordered list of sensed intervals) is selected for analysis. If the answer to the determination at step 420 is No, then flow goes to step 422, which is discussed below.

Steps 404 through 420, summarized above, are used to remove true R-R intervals from the ordered list of intervals being analyzed, which is accomplished by removing all intervals that are within a corresponding threshold (e.g., 10%) of the sum of the immediately preceding two intervals within the list, or that are within a corresponding threshold (e.g., 10%) of the sum of the immediately following two intervals within the list, as such intervals are likely true R-R intervals with a neighboring over-sensed R-R interval. While it is likely that the same threshold (e.g., 10%) is used at both step 410 and step 416, that need not be the case. The threshold used at step 410 and/or 416 can be a percentage, such as 10%, or some higher or lower percentage. Alternatively, the threshold used at step 410 and/or 416 can be a specified value, e.g., 80 milliseconds (ms), or some higher or lower value. Other variations are also possible, and within the scope of the embodiments described herein.

Returning to the discussion of step 422, step 422 involves determining a mean or median of the durations of the sensed intervals already identified as true R-R intervals (at instances of steps 418). Accordingly, at step 422 a likely duration of true R-R intervals is determined. Flow then goes to step 424 in FIG. 4B. Step 424 involves identifying (aka classifying) as a true R-R interval, each sensed interval (in the remaining ordered list of sensed intervals) that has a duration that is within a corresponding threshold (e.g., 10%) of the mean or median determined at step 422. Thus, R-R intervals are also identified as true R-R intervals if they are within a corresponding threshold (e.g., 10%) of the mean or median of the previously identified true R-R intervals. The threshold used at step 424 can be a percentage, such as 10%, or some higher or lower percentage. Alternatively, the threshold used at step 424 can be a specified value, e.g., 80 milliseconds (ms), or some higher or lower value. Other variations are also possible, and within the scope of the embodiments described herein. It can be appreciated from the description herein that the terms "identified" and "classified", and the terms "identify" and "classify", are often referred to interchangeably herein.

Step 426 involves removing from the ordered list of sensed intervals, each sensed interval that was already identified as being a true R-R interval at an instance of step 418 or 424, to thereby produce a remaining ordered list of sensed intervals. Step 428 then involves classifying (aka identifying) intervals in the remaining ordered list of intervals as either a short interval or a long interval. For an example, an interval (in the remaining ordered list of sensed intervals) can be classified as a short interval when a duration of the interval is shorter than an immediately following interval in the remaining ordered list of sensed intervals; and an interval (in the remaining ordered list of sensed intervals) can be classified as a long interval when a duration of the interval is longer than an immediately following interval in the remaining ordered list of sensed intervals. Other ways of classifying intervals as short or long intervals are also possible and within the scope of the embodiments described herein. For example, rather than (or in addition to) comparing a duration of an interval to the duration of the following interval, the duration of the interval can be compared to the duration of the preceding interval. In certain embodiments, the first and/or last interval (in the remaining ordered list of sensed intervals) is removed or ignored.

Step 430 involves producing an ordered list of the short intervals. This can be accomplished, for example, by removing all the long intervals (identified at step 428) from the remaining ordered list of sensed intervals (produced at step 426). This can alternatively be accomplished by creating a new ordered list that just includes the short intervals identified at step 428. Other variations are also possible and within the scope of the embodiments described herein.

Step 432 involves selecting an interval (from the ordered list of short intervals produced at step 430) to analyze. The first time step 432 is performed (for an ordered list of short intervals), the first interval in the ordered list is selected. The second time step 432 is performed (for the ordered list of short intervals), the second interval in the ordered list is selected, and so on.

At step 434 there is a determination of whether the interval (selected for analysis at step 432) is the first interval in the ordered list of short intervals. If the selected interval is the first interval (i.e., if the answer to the determination at step 434 is Yes), then flow goes back to step 432 and the next interval is selected for analysis. If the selected interval is not the first interval (i.e., if the answer to the determination at step 434 is No), then flow goes to step 436.

At step 436 there is a determination of whether the interval (selected for analysis at step 432) is the last interval in the ordered list of short intervals. If the selected interval is the last interval (i.e., if the answer to the determination at step 436 is Yes), then flow skips to step 452. If the selected interval is not the last interval (i.e., if the answer to the determination at step 436 is No), then flow goes to step 438.

Step 438 involves determining a difference between the duration of the selected short interval and the duration of the immediately preceding short interval. At step 440 there is a determination of whether the difference determined at step 438 is within a corresponding threshold (e.g., 10%) of the immediately preceding short interval. If the answer to the determination at step 440 is No, then flow returns to step 432 where the next short interval to analyze is selected. If the answer to the determination at step 440 is Yes, then flow goes to step 442. Steps 438 and 440 are used to test the short interval variability criteria, because the "short" intervals that truly correspond to oversensing (i.e., that are over-sensed R-R intervals) should have low interval-interval variability, e.g., quantified by a difference from the previous "short" interval of less than 10% or some other specified threshold.

Step 442 involves determining a difference between the duration of the selected short interval and the duration of the immediately following long interval. At step 444 there is a determination of whether the difference determined at step 442 is greater than a corresponding threshold (e.g., 5%) of the immediately following long interval. If the answer to the determination at step 444 is No, then flow returns to step 432 where the next short interval to analyze is selected. If the answer to the determination at step 444 is Yes, then flow goes to step 446. The threshold used at step 444 can be a percentage, such as 5%, or some higher or lower percentage. Alternatively, the threshold used at step 446 can be a specified value, e.g., 20 milliseconds (ms), or some higher or lower value. Other variations are also possible, and within the scope of the embodiments described herein. Steps 442 and 444 are used to test the short-long interval discrepancy, because a short interval that truly correspond to oversensing should differ from the next long interval by more than 5% or some other specified threshold.

Step 446 involves determining whether the duration of the selected short interval is less than a corresponding threshold, e.g., 444 ms (i.e., greater than 135 bpm). If the answer to the determination at step 446 is No, then flow returns to step 432 where the next short interval to analyze is selected. If the answer to the determination at step 446 is Yes, then flow goes to step 448. Step 446 is used to test the short interval duration, which handles the possibility that all of the above criteria could be satisfied by slow, yet variable, heart rates. During true oversensing, a short interval should correspond to a very fast heart rate, which is tested for at step 446.

At step 448 the short interval (for which the answers to the determinations at step 440, 444, and 446 were all Yes) is identified (aka classified) as an over-sensed R-R interval. This is because the interval satisfied the short interval variability criteria, the short-long interval discrepancy criteria, and the short interval duration criteria, which were discussed above.

At step 450 there is a determination of whether there is at least one additional short interval (in the ordered list of short intervals) to analyze. If the answer to the determination at step 450 is Yes, then flow returns to step 432 where the next short interval (in the ordered list of short intervals) is selected for analysis. If the answer to the determination at step 450 is No, then flow goes to step 452 in FIG. 4C, which is discussed below.

Figure 4C:
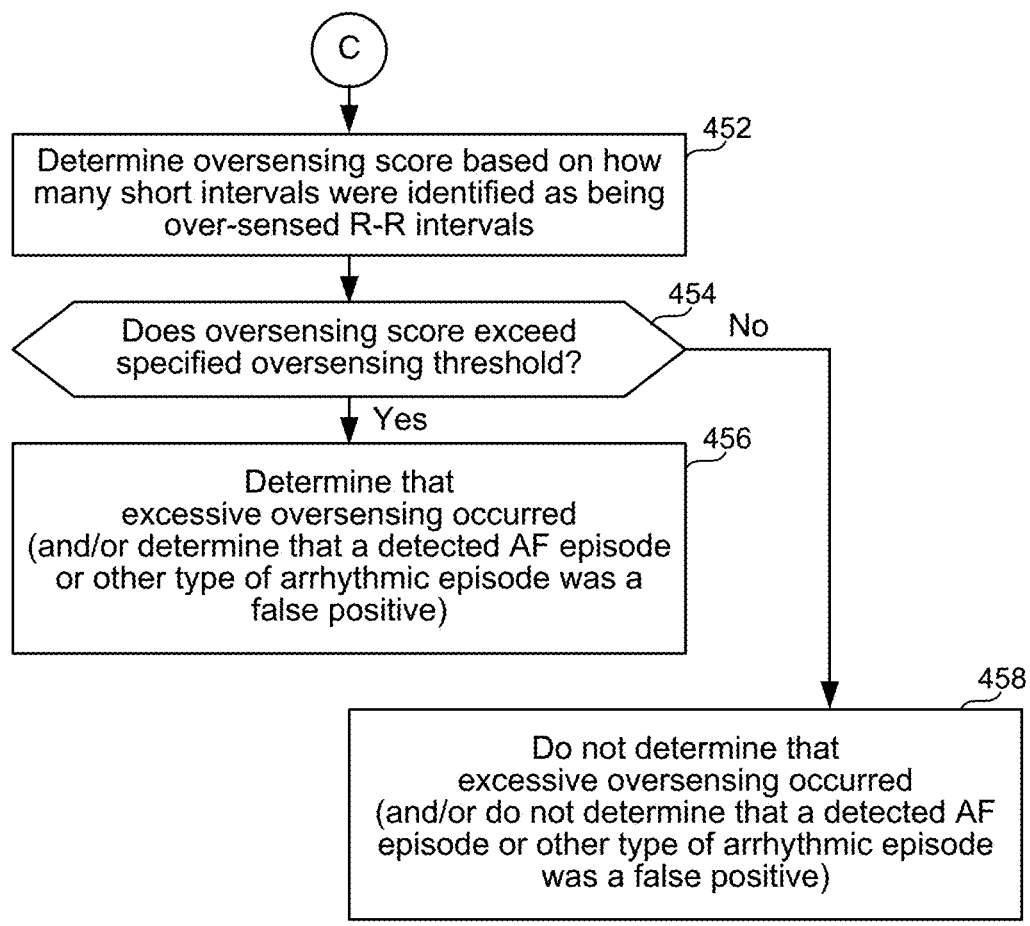

Referring to FIG. 4C, step 452 involves determining an oversensing score based on how many short intervals were identified as being over-sensed R-R intervals (at instances of step 448). In accordance with certain embodiments, the oversensing score is determined by determining what percentage of all of the sensed intervals classified as a short interval were identified as being an over-sensed R-R interval. Another way to calculate the oversensing score is using the equation Oversensing Score (OS)=2×[the total number of sensed intervals classified as a short interval that were identified as being an over-sensed R-R interval]/[total number of all intervals]. The factor of "2" in this equation accounts for the fact that each "short" interval also has a paired "long" interval, so it should count as 2 of the total intervals when calculating a percent. In other words, both intervals associated with (i.e., before and after) an oversensed P- or T-wave are counted. Other variations are also possible and within the scope of the embodiments described herein.

At step 454 there is a determination of whether the oversensing score (determined at step 452) exceeds a corresponding threshold (e.g., 50%). If the oversensing score exceeds the corresponding threshold (e.g., if more than 50% of the short intervals were classified as being over-sensed intervals), then flow goes to step 456. At step 456 there is a determination or conclusion that excessive oversensing had occurred. Such a determination or conclusion can be used to determine that a detected AF episode (or other type of arrhythmic episode) that was detected based on the sensed intervals was a false positive. If the oversensing score does not exceed the corresponding threshold (e.g., if less than 50% of the short intervals were classified as being oversensed intervals), then flow goes to step 458, and there is no conclusion or determination that excessive oversensing occurred. In accordance with certain embodiments, different corresponding thresholds can be used for different types of tachycardias. For example, the corresponding threshold to which an oversensing score is compared when determining whether the detection of an AF episode was a false positive detection could be 50%, and the corresponding threshold to which an oversensing score is compared when determining whether the detection of a VT episode was a false positive detection could be 70%.

In accordance with certain embodiments, an IMD may perform the method described above with reference to FIG. 4 in response to an AF episode (or some other type of arrhythmic episode) being detected. The detection of an AF episode can also be referred to as an AF trigger. Such an IMD may be configured to transmit, to an external device that is communicatively coupled to a patient care network, data corresponding to an AF episode (or other type of arrhythmic episode) that is detected by the IMD. In certain such embodiments, the IMD does not (is prevented from) transmitting (to the external device that is communicatively coupled to the patient care network) data corresponding to an AF episode (or other type of arrhythmic episode) that is detected by the IMD, but is thereafter determined by the IMD as being a false positive detection.

In accordance with certain embodiments, the medical device (e.g., IMD) that performs the method described above with reference to FIG. 4 may monitor the HR of a patient based on intervals identified from a segment of an EGM or ECG, and the medical device can determine based on the results of the method whether a monitored HR is inaccurate due to oversensing and thus should be ignored or recalculated. For an example, if an oversensing score exceeds a corresponding threshold, the medical device can conclude that a HR that was determined based on sensed interval is inaccurate and should not be used, or should be recalculated.

In accordance with certain embodiments, after identifying true R-R intervals (e.g., at instances of steps 418 and/or 424) and identifying (aka classifying) individual over-sensed R-R intervals short or long intervals, pairs of over-sensed R-R intervals can be combined to identify further true R-R intervals. For example, a short interval (e.g., R-T interval) and a following long interval (e.g., T-R interval) can be summed to produce a calculated true R-R interval. For another example, adjacent R-P and P-R intervals can be summed to produce a calculated true R-R interval. A corrected ordered list of sensed intervals can then be produced that includes the true R-R intervals (e.g., identified at instances of steps 418 and/or 424) and the further true R-R intervals identified by summing appropriate pairs of over-sensed R-R intervals. HR monitoring and/or monitoring for an arrhythmic episode can then be based on the corrected ordered list of sensed intervals.

An implementation of an embodiment of the present technology described above was tested to determine whether and to what extend the present technology can be used to reduce the reporting of false positive AF detections. EGM segments corresponding to a total of 5,989 detected AF episodes (that were detected by Confirm Rx™ ICMs) were manually adjudicated as either "true" or "false" positive AF detections. Among other characteristics, the heart rate (HR), heart rate variability (HRV), lack of heart rate patterns, lack of visible P-waves, variable R-wave morphology, and P:R ratio were used for the manual adjudication. Note that the manual adjudication relied on both the R-R intervals and the EGM signal morphology, and required thousands of human-hours to perform. Using only the R-R interval values in the 30 seconds preceding each AF detection trigger, an embodiment of the present technology described above was used to automatically calculate the "oversensing score" of all episodes in under 10 seconds. Of the 5,989 episodes, 1469 episodes (24.5%) were adjudicated as true AF episodes (i.e., as true positives), and the remaining 4,520 episodes (75.5%) were adjudicated as non-AF episodes (i.e., as false positives). Of the 4520 manually adjudicated non-AF episodes (i.e., false positive AF detections), 303 (6.7%) were flagged by the present technology as oversensing (and thus, as being false positives) because the oversensing score was greater than a 50% threshold. This corresponds to a potential 6.7% reduction in false positives using an interval-based embodiment of the present technology. Note that false positive AF episodes can be the result of many other phenomena besides oversensing, such as, but not limited to, R-wave undersensing, noise, ventricular tachycardia, PVCs, or atrial flutter. Overall, 305 detected AF episodes were flagged as false positives using an embodiment of the present technology. Of those, 303 detected AF episodes (99.3%) were indeed manually adjudicated as non-AF episodes. Beneficially, only 2 of the 1469 detected AF episodes (0.1%) were incorrectly flagged as false positives. Embodiments of the present technology can be used together with other types of technology that can be used to identify further false positives, or more generally, excessive oversensing.

The specific thresholds used to test the performance of embodiments of the present technology (e.g. 10% interval stability, 5% interval discrepancy, 135 bpm heart rate lower limit, 50% oversensing score threshold) and mentioned above can be more systematically optimized for a broader patient population, or for individual patients. Accordingly, embodiments of the present technology described herein should not be limited to use with the exemplary thresholds described herein.

While embodiments of the present technology described herein have often been described as being used to determine whether a detected AF episode was a false positive detection, such embodiments can alternatively or additionally be used to determine whether detections of other types of supraventricular tachycardia episodes, and/or detections of ventricular tachycardia (VT) episodes, are false positive detections.

The specific window or ordered list of sensed intervals that is analyzed to determine whether a detected tachycardia episode was a false positive detection may depend on the specific type of tachycardia that was detected. For example, where an AF episode was detected, the ordered list of sensed intervals that is analyzed can include sensed intervals corresponding to a period of time (e.g., 30 seconds) preceding and leading up to the detected AF episode. By contrast, where a VT episode was detected, the ordered list of sensed intervals that is analyzed can be those sensed intervals spanning and inclusive of the first and last tachy-classified sensed intervals. Other variations are also possible and within the scope of the embodiments described herein.

Embodiments of the present technology described herein can be used with various types of IMDs, including, but not limited to, an insertable cardiac monitor (ICM), a cardiac pacemaker to which one or more leads is/are attached, a leadless cardiac pacemaker (LCP), or an implantable cardioverter defibrillator (ICD). Such an ICD can be a transvascular ICD, or a nonvascular ICD, wherein the nonvascular ICD can be a subcutaneous (SubQ) ICD. Where embodiments of the present technology are implemented by an ICM, such embodiments can be used, e.g., to reduce the number of false positive AF detections that are transmitted from the ICM to a patient care network for clinician review. This is beneficially because false positive AF detections are highly undesirable, as the burden of sorting through large numbers of clinically irrelevant episodes of AF can be time consuming and costly. Where embodiments of the present technology are used by an ICD, or by an IMD in communication with an ICD, such embodiments can reduce how often anti-tachycardia pacing (ATP) and/or defibrillation shocks are delivered in response to false positive tachycardia detections. This is beneficial because defibrillation shocks are typically painful, and delivering such shocks when patient is awake in response to false positive tachycardia detections subjects the patient to unnecessary painful or uncomfortable shocks and may prematurely deplete the energy stored in a battery.

Figure 5:
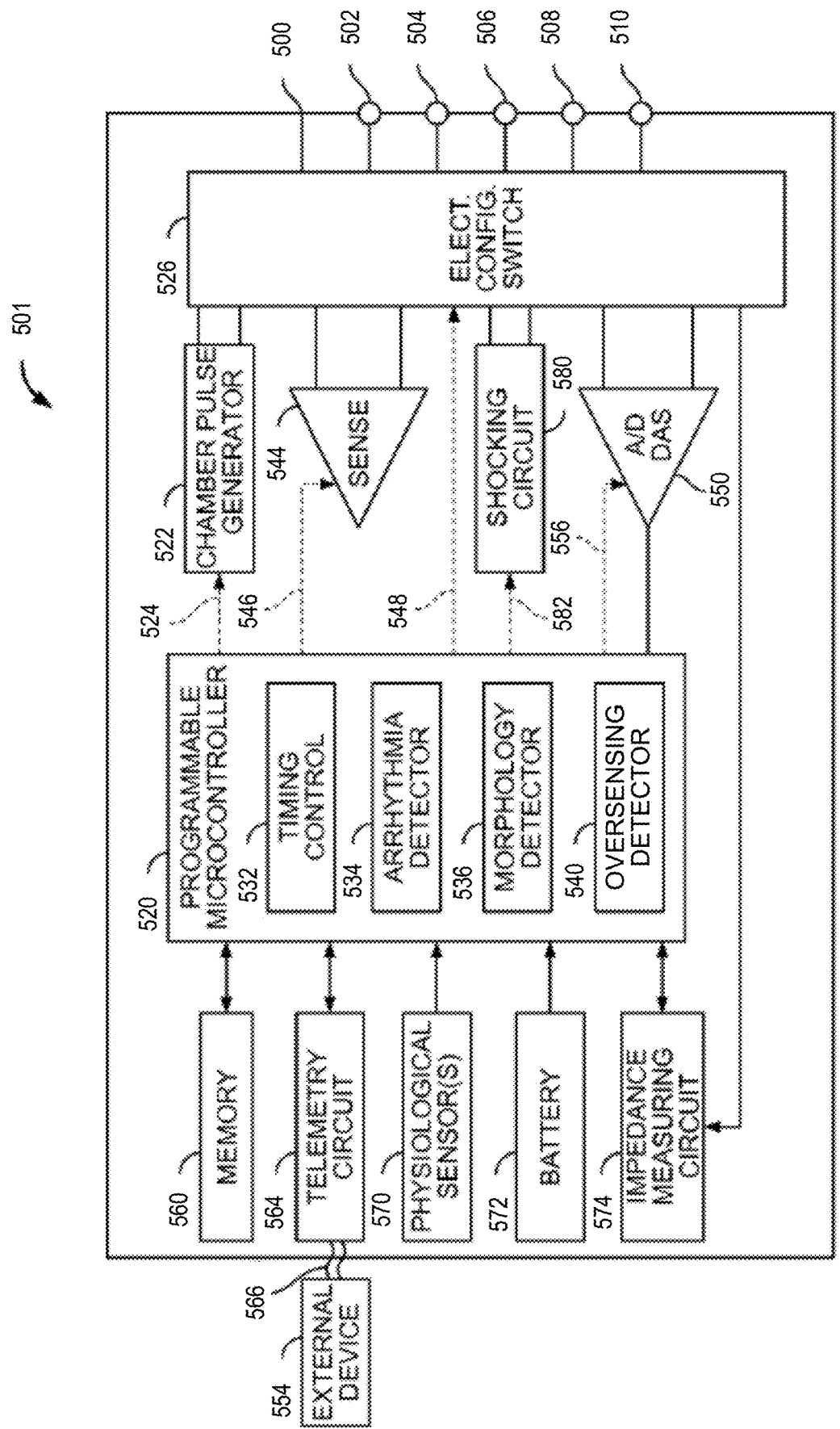
FIG. 5 shows a block diagram of one embodiment of an IMD that is implanted into a patient in accordance with certain embodiments of the present technology.

FIG. 5 shows a block diagram of one embodiment of an IMD that is implanted into a patient in accordance with a certain embodiment of the present technology. The IMD 501 may be implemented as a full-function biventricular pacemaker, equipped with both atrial and ventricular sensing and pacing circuitry for four chamber sensing and stimulation therapy (including both pacing and shock treatment). Optionally, the IMD 501 may provide full-function cardiac resynchronization therapy. Alternatively, the IMD 501 may be implemented with a reduced set of functions and components. For instance, the IMD may be implemented without pacing, e.g., if the IMD is an ICM. The IMD 501 can be coupled to one or more leads for single chamber or multi-chamber pacing and/or sensing. Alternatively, the IMD 501 can be an LCP that includes electrodes located on or very close to a housing 500 of the IMD 501.

The IMD 501 has a housing 500 to hold the electronic/computing components. The housing 500 (which is often referred to as the "can", "case", "encasing", or "case electrode") may be programmably selected to act as the return electrode for certain stimulus modes. The housing 500 may further include a connector (not shown) with a plurality of terminals 502, 504, 506, 508, and 510. The terminals may be connected to electrodes that are located in various locations on the housing 500 or to electrodes located on leads. The IMD 501 includes a programmable microcontroller 520 that controls various operations of the IMD 501, including cardiac monitoring and/or stimulation therapy. The microcontroller 520 includes a microprocessor (or equivalent control circuitry), RAM and/or ROM memory, logic and timing circuitry, state machine circuitry, and I/O circuitry.

The IMD 501 further includes a pulse generator 522 that generates stimulation pulses and communication pulses for delivery by one or more electrodes coupled thereto. The pulse generator 522 is controlled by the microcontroller 520 via a control signal 524. The pulse generator 522 may be coupled to the select electrode(s) via an electrode configuration switch 526, which includes multiple switches for connecting the desired electrodes to the appropriate I/O circuits, thereby facilitating electrode programmability. The switch 526 is controlled by a control signal 528 from microcontroller 520.

In the embodiment of FIG. 5, a single pulse generator 522 is illustrated. Optionally, the IMD may include multiple pulse generators, similar to the pulse generator 522, where each pulse generator is coupled to one or more electrodes and controlled by the microcontroller 520 to deliver select stimulus pulse(s) to the corresponding one or more electrodes.

The microcontroller 520 is illustrated as including timing control circuitry 532 to control the timing of the stimulation pulses (e.g., pacing rate, atrio-ventricular (AV) delay, atrial interconduction (A-A) delay, or ventricular interconduction (V-V) delay, etc.). The timing control circuitry 532 may also be used for the timing of refractory periods, blanking intervals, noise detection windows, evoked response windows, alert intervals, marker channel timing, and so on. The microcontroller 520 also has an arrhythmia detector 534 for detecting arrhythmia conditions and a morphology detector 536. Although not shown, the microcontroller 520 may further include other dedicated circuitry and/or firmware/software components that assist in monitoring various conditions of the patient's heart and managing pacing therapies. The microcontroller 520 is also shown as including an oversensing detector 540, which can be used to perform the embodiments of the present technology described above with reference to FIGS. 1-4. The oversensing detector 540 can more generally be implemented using hardware, software, firmware, and/or combinations thereof. The microcontroller can include a processor. The microcontroller, and/or the processor thereof, can be used to perform the methods of the present technology described herein.

The IMD 501 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 520, or as software/firmware instructions programmed into and executed by the microcontroller 520. Alternatively, the modem may reside separately from the microcontroller as a standalone component.

The IMD 501 includes a sensing circuit 544 selectively coupled to one or more electrodes, that perform sensing operations, through the switch 526 to detect the presence of cardiac activity in the right chambers of the heart. The sensing circuit 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 526 determines the sensing polarity of the cardiac signal by selectively closing the appropriate switches. In this way, the clinician may program the sensing polarity independent of the stimulation polarity.

The output of the sensing circuit 544 is connected to the microcontroller 520 which, in turn, triggers or inhibits the pulse generator 522 in response to the presence or absence of cardiac activity. The sensing circuit 544 receives a control signal 546 from the microcontroller 520 for purposes of controlling the gain, threshold, polarization charge removal circuitry (not shown), and the timing of any blocking circuitry (not shown) coupled to the inputs of the sensing circuitry.

In the embodiment of FIG. 5, a single sensing circuit 544 is illustrated. Optionally, the IMD may include multiple sensing circuits, similar to the sensing circuit 544, where each sensing circuit is coupled to one or more electrodes and controlled by the microcontroller 520 to sense electrical activity detected at the corresponding one or more electrodes. The sensing circuit 544 may operate in a unipolar sensing configuration or in a bipolar sensing configuration.

The IMD 501 further includes an analog-to-digital (ND) data acquisition system (DAS) 550 coupled to one or more electrodes via the switch 526 to sample cardiac signals across any pair of desired electrodes. Data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). Data acquisition system 550 is controlled by a control signal 556 from the microcontroller 520.

The microcontroller 520 is coupled to a memory 560 by a suitable data/address bus. The programmable operating parameters used by the microcontroller 520 are stored in memory 560 and used to customize the operation of the IMD 501 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 501 may be non-invasively programmed into memory 560 through a telemetry circuit 564 in telemetric communication via a communication link 566 with an external device 554. The telemetry circuit 564 allows intracardiac electrograms and status information relating to the operation of the IMD 501 (as contained in the microcontroller 520 or memory 560) to be sent to the external device 554 through the communication link 566.

The IMD 501 can further include magnet detection circuitry (not shown), coupled to the microcontroller 520, to detect when a magnet is placed over the unit. A magnet may be used by a clinician to perform various test functions of IMD 501 and/or to signal the microcontroller 520 that the external device 554 is in place to receive or transmit data to the microcontroller 520 through the telemetry circuit 564.

The IMD 501 can further include one or more physiological sensors 570.

Such sensors are commonly referred to as "rate-responsive" sensors because they are typically used to adjust pacing stimulation rates according to the exercise state of the patient. However, the physiological sensor(s) 570 may further be used to detect changes in cardiac output, changes in the physiological condition of the heart, or diurnal changes in activity (e.g., detecting sleep and wake states). Signals generated by the physiological sensor(s) 570 are passed to the microcontroller 520 for analysis. The microcontroller 520 responds by adjusting the various pacing parameters (such as rate, AV Delay, V-V Delay, etc.) at which the atrial and ventricular pacing pulses are administered. While shown as being included within the IMD 501, one or more physiological sensor(s) 570 may be external to the IMD 501, yet still be implanted within or carried by the patient. Examples of physiologic sensors include sensors that, for example, sense respiration rate, pH of blood, ventricular gradient, activity, position/posture, minute ventilation (MV), and so forth.

A battery 572 provides operating power to all of the components in the IMD 501. The battery 572 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 572 also desirably has a predictable discharge characteristic so that elective replacement time can be detected. As one example, the IMD 501 employs lithium/silver vanadium oxide batteries.

The IMD 501 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used. In this embodiment the IMD 501 further includes a shocking circuit 580 coupled to the microcontroller 520 by a data/address bus 582.

The embodiments of the present technology described above were primarily described as being used with an implantable medical device or system that monitors HR and/or for one or more types of arrhythmic episodes based on sensed intervals, which as noted above can be, e.g., true R-R intervals or over-sensed R-R intervals. Such embodiments of the present technology can alternatively be used with a non-implantable device or system (aka an external device or system) that includes at least two electrodes in contact with a person's skin and is used to monitor HR and/or for one or more types of arrhythmic episodes based on sensed intervals. More specifically, such embodiments can alternatively be used with or be implemented by a user wearable device, such as a wrist worn device, or a user wearable device designed to be worn on one or more other portions of a person's body besides a wrist, e.g., on an ankle, an upper arm, or a chest, but not limited thereto. Such a user wearable device can include electrodes that are configured to contact a person's skin, sensing circuitry coupled to the electrodes and configured to obtain a signal indicative of electrical activity of a patient's heart, and at least one of a processor or controller that is configured to perform one or more of the algorithms described above. Such a user wearable device (or more generally an external device or system) can monitor for AF and/or other types of arrhythmia(s) and determine when there is a false positive detection. Additionally, or alternatively, such a user wearable device (or more generally an external device or system) can monitor a person's HR and determine when measures of HR are likely inaccurate due to oversensing. A user wearable device can both obtain a signal indicative of electrical activity of a patient's heart and monitor a person's HR and/or for arrhythmia(s) based on intervals obtained from the obtained signal. Alternatively, a user wearable device can be communicatively coupled to another external device, such as a smartphone or tablet computer, and the other external device can obtain the signal from the user wearable device and monitor a person's HR and/or for arrhythmia(s) based on intervals. The user wearable device or other external device or system can determine when there may be a false positive and/or when a measured HR may be inaccurate due to oversensing. Other implementations of such an external device or system are also possible and within the scope of the embodiments described herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 4. For another example, it is possible to change the boundaries of some of the blocks shown in FIG. 5.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for use by a device or system that monitors heart rate and/or for one or more types of arrhythmic episodes, the method comprising:
   (a) obtaining an ordered list of sensed intervals, wherein each of the sensed intervals has a respective duration;
   (b) identifying as a true R-R interval, each said sensed interval having a duration that is within a first specified threshold of either (i) a sum of the durations of an immediately preceding two intervals in the ordered list of sensed intervals, or (ii) a sum of the durations of an immediately following two intervals in the ordered list of sensed intervals;
   (c) identifying as a true R-R interval, each said sensed interval having a duration that is within a second specified threshold of a mean or median of the durations of the sensed intervals already identified as true R-R intervals, wherein the second specified threshold may or may not be the same as the first specified threshold;
   (d) removing, from the ordered list of sensed intervals, each of the sensed intervals that was identified as being a true R-R interval, to thereby produce a remaining ordered list of sensed intervals;
   (e) classifying individual intervals in the remaining ordered list of sensed intervals as either a short interval or a long interval; and
   (f) identifying one or more over-sensed R-R intervals, in the remaining ordered list of sensed intervals, based on results of the classifying individual intervals in the remaining ordered list of sensed intervals as either a said short interval or a said long interval.

2. The method of claim 1, wherein the (f) identifying one or more over-sensed R-R intervals comprises, for at least one said sensed interval classified as a said short interval in the remaining ordered list of sensed intervals, identifying the sensed interval as an over-sensed R-R interval when all of the following are true:
   (f.1) a difference between a duration of the sensed interval that was classified as a said short interval and a duration of an immediately preceding sensed interval that was classified as a said short interval is within a third specified threshold;
   (f.2) a difference between the duration of the sensed interval that was classified as a said short interval and a duration of an immediately following sensed interval that was classified as a said long interval is greater than a fourth specified threshold; and
   (f.3) the duration the sensed interval that was classified as a said short interval is less than a fifth specified threshold.

3. The method of claim 2, wherein the (f) identifying one or more over-sensed R-R intervals based on results of the classifying each of the intervals in the remaining ordered list of sensed intervals as either a said short interval or a said long interval, further comprises:

for each sensed interval classified as a said long interval, in the remaining ordered list of sensed intervals, identifying the sensed interval as an over-sensed R-R interval if an immediately preceding or following sensed interval classified as a said short interval has been identified as an over-sensed R-R interval.

4. The method of claim 2, further comprising:
(g) determining an oversensing score based on how many of the sensed intervals classified as a said short interval were identified as being an over-sensed R-R interval; and
(h) determining that a detected AF episode or other type of arrhythmic episode was a false positive detection when the oversensing score exceeds a specified oversensing threshold.

5. The method of claim 4, wherein:
the specified oversensing threshold comprises a specified percentage threshold;
the (g) determining the oversensing score comprises determining what percentage of all of the sensed intervals classified as a said short interval were identified as being an over-sensed R-R interval; and
the (h) determining that a detected AF episode or other type of arrhythmic episode was a false positive detection occurs when the determined percentage exceeds the specified percentage threshold.

6. The method of claim 1, wherein steps (a) through (f) are performed by an implantable medical device (IMD) in response to an AF episode or other type of arrhythmic episode being detected by the IMD, and further comprising:
(g) the IMD determining, based on results of steps (a) through (f), whether the AF episode or other type of arrhythmic episode that was detected by the IMD was a false positive detection.

7. The method of claim 6, wherein the IMD is configured to transmit, to an external device that is communicatively coupled to a patient care network, data corresponding to an AF episode or other type of arrhythmic episode that is detected by the IMD, and wherein the method further comprises:
(h) the IMD preventing or limiting transmitting, to the external device that is communicatively coupled to the patient care network, data corresponding to an AF episode or other type of arrhythmic episode that is detected by the IMD but is thereafter determined by the IMD as being a false positive detection.

8. The method of claim 6, wherein the (a) obtaining the ordered list of sensed intervals comprises:
(a.1) obtaining an electrogram (EGM) segment corresponding to a period of time preceding and leading up to the AF episode or other type of arrhythmic episode that was detected;
(a.2) identifying potential R-waves within the EGM segment; and
(a.3) determining intervals between consecutive ones of the potential R-waves to thereby produce the ordered list of sensed intervals.

9. The method of claim 6, wherein the IMD comprises one of the following:
an insertable cardiac monitor (ICM);
a cardiac pacemaker to which one or more leads is/are attached;
a leadless cardiac pacemaker (LCP); or
an implantable cardioverter defibrillator (ICD).

10. The method of claim 1, wherein the (e) classifying individual intervals, in the remaining ordered list of sensed intervals, as either a short interval or a long interval comprises:
classifying a said interval, in the remaining ordered list of sensed intervals, as a short interval when a duration of the said interval is shorter than an immediately following interval in the remaining ordered list of sensed intervals; and
classifying a said interval, in the remaining ordered list of sensed intervals, as a long interval when a duration of the said interval is longer than an immediately following interval in the remaining ordered list of sensed intervals.

11. The method of claim 1, wherein steps (a) through (f) are performed by a device that monitors heart rate (HR) based on intervals identified from a segment of an electrogram (EGM) or electrocardiogram (ECG), and further comprising:
(g) the device determining, based on results of steps (a) through (f), whether a monitored HR is inaccurate due to oversensing and thus should be ignored or recalculated.

12. The method of claim 1, further comprising, after identifying true R-R intervals at steps (b) and (c) and identifying over-sensed R-R intervals at step (f):
combining pairs of over-sensed R-R intervals to identify further true R-R intervals;
producing a corrected ordered list of sensed intervals that includes the true R-R intervals identified at steps (b) and (c), and includes the further true R-R intervals identified by combining pairs of over-sensed R-R intervals; and
monitoring heart rate and/or for an arrhythmic episode based on the corrected ordered list of sensed intervals.

13. A device, comprising:
one or more electrodes;
a sensing circuitry coupled to the one or more electrodes and configured to obtain a signal indicative of electrical activity of a patient's heart; and
at least one of a processor or controller configured to
obtain an ordered list of sensed intervals, based on the signal indicative of electrical activity of the patient's heart, wherein each of the sensed intervals has a respective duration;
identify as a true R-R interval, each said sensed interval having a duration that is within a first specified threshold of either (i) a sum of the durations of an immediately preceding two intervals in the ordered list of sensed intervals, or (ii) a sum of the durations of an immediately following two intervals in the ordered list of sensed intervals;
identify as a true R-R interval, each said sensed interval having a duration that is within a second specified threshold of a mean or median of the durations of the sensed intervals already identified as true R-R intervals, wherein the second specified threshold may or may not be the same as the first specified threshold;
remove, from the ordered list of sensed intervals, each of the sensed intervals that was identified as being a true R-R interval, to thereby produce a remaining ordered list of sensed intervals;
classify individual intervals, in the remaining ordered list of sensed intervals, as either a short interval or a long interval; and
identify one or more over-sensed R-R intervals, in the remaining ordered list of sensed intervals, based on an analysis of at least the short intervals in the remaining ordered list of sensed intervals.

14. The device of claim 13, wherein the at least one of a processor or controller is/are further configured to:
   determine an oversensing score based on how many of the sensed intervals classified as a said short interval were identified as being an over-sensed R-R interval; and
   determine, based on the oversensing score, whether a detected AF episode or other type of arrhythmic episode was a false positive detection.

15. The device of claim 13, wherein the at least one of a processor or controller is/are further configured to:
   combine pairs of over-sensed R-R intervals to identify further true R-R intervals;
   produce a corrected ordered list of sensed intervals including true R-R intervals, at least some of which are identified by combining pairs of over-sensed R-R intervals; and
   monitor heart rate and/or for an arrhythmic episode based on the corrected ordered list of sensed intervals.

16. The device of claim 13, further comprising a transceiver configured to wireless communicate with an external device, and wherein the at least one of a processor or controller is/are further configured to interact with the transceiver to:
   cause data corresponding to an atrial fibrillation (AF) episode or other type of arrhythmic episode that is detected by the device be selectively transmitted to the external device; and
   prevent data corresponding to an AF episode or other type of arrhythmic episode that is detected by the device, but is thereafter determined by the device as being a false positive detection, from being transmitted to the external device.

17. The device of claim 13, wherein the device comprises one of the following:
   a user wearable device;
   an insertable cardiac monitor (ICM);
   a cardiac pacemaker to which one or more leads is/are attached;
   a leadless cardiac pacemaker (LCP); or
   an implantable cardioverter defibrillator (ICD).

18. A method for use by a device or system that monitors heart rate and/or for one or more types of arrhythmic episodes, the method comprising:
   identifying true R-R intervals within an ordered list of sensed intervals and removing from the ordered list of sensed intervals each of the sensed intervals that was identified as being a true R-R interval, to thereby produce a remaining ordered list of sensed intervals;
   classifying individual intervals, in the remaining ordered list of sensed intervals, as either a short interval or a long interval;
   identifying which individual intervals, which have been classified as a said short interval, are over-sensed R-R intervals; and
   determining, based on results the identifying which individual intervals are over-sensed R-R intervals, whether a monitored heart rate or arrhythmic episode detection is inaccurate due to oversensing and thus should be ignored or recalculated.

19. The method of claim 18, wherein the determining, based on results the identifying which individual intervals are over-sensed R-R intervals, whether a monitored heart rate or arrhythmic episode detection is inaccurate due to oversensing and thus should be ignored or recalculated, comprises:
   determining an oversensing score based on how many of the sensed intervals classified as a said short interval were identified as being an over-sensed R-R interval; and
   determining, based on the oversensing score, whether a monitored heart rate of arrhythmic episode detection is inaccurate due to oversensing and thus should be ignored or recalculated.

20. The method of claim 18, wherein after there is a determination that a monitored heart rate or arrhythmic episode detection is inaccurate due to oversensing and thus should be ignored or recalculated, the method further comprises:
   combining pairs of over-sensed R-R intervals to identify further true R-R intervals;
   producing a corrected ordered list of sensed intervals including true R-R intervals, at least some of which are identified by combining pairs of over-sensed R-R intervals; and
   monitoring heart rate and/or for an arrhythmic episode based on the corrected ordered list of sensed intervals.

* * * * *